US012018228B2

(12) United States Patent
Cocito Armanino et al.

(10) Patent No.: US 12,018,228 B2
(45) Date of Patent: Jun. 25, 2024

(54) ALKOXYBENZALDEHYDE DERIVATIVES AND PRECURSORS THEREOF

(71) Applicant: Givaudan SA, Vernier (CH)

(72) Inventors: Nicolas Cocito Armanino, Baden (CH); Corinne Baumgartner, Fällanden (CH); Felix Flachsmann, Duebendorf (CH)

(73) Assignee: Givaudan SA, Vernier (CH)

( * ) Notice: Subject to any disclaimer, the term of this patent is extended or adjusted under 35 U.S.C. 154(b) by 582 days.

(21) Appl. No.: 17/289,950

(22) PCT Filed: Oct. 30, 2019

(86) PCT No.: PCT/EP2019/079605
§ 371 (c)(1),
(2) Date: Apr. 29, 2021

(87) PCT Pub. No.: WO2020/089274
PCT Pub. Date: May 7, 2020

(65) Prior Publication Data
US 2022/0002634 A1 Jan. 6, 2022

(30) Foreign Application Priority Data
Oct. 31, 2018 (GB) ..................................... 1817785

(51) Int. Cl.
C11B 9/00 (2006.01)
C11D 3/20 (2006.01)
C11D 3/50 (2006.01)

(52) U.S. Cl.
CPC .......... *C11B 9/0061* (2013.01); *C11D 3/2068* (2013.01); *C11D 3/2072* (2013.01); *C11D 3/50* (2013.01)

(58) Field of Classification Search
CPC ... C11B 9/0061; C07D 309/14; C07D 317/50; C07D 295/185; C07D 257/04; C07C 43/23; C07C 43/215; C07C 47/575; C07C 2602/08; C11D 3/50; C11D 3/2072
USPC .......................................... 512/21, 20, 8, 1
See application file for complete search history.

(56) References Cited

U.S. PATENT DOCUMENTS 5,756,853 A 5/1998 Metivier et al.
6,117,833 A 9/2000 Racherla et al.
2013/0316938 A1 11/2013 Baumgartner et al.
2016/0122271 A1 5/2016 Indradas et al.
2017/0283737 A1* 10/2017 Indradas ................. C11D 3/001
2018/0016521 A1 1/2018 Indradas et al.

FOREIGN PATENT DOCUMENTS

| CN | 104926633 A | 9/2015 |
| JP | H0352839 A | 3/1991 |
| WO | 9721794 A1 | 7/1997 |
| WO | 2000/36070 A1 | 6/2000 |
| WO | 0036064 A1 | 6/2000 |
| WO | 2012/085287 A1 | 6/2012 |

OTHER PUBLICATIONS

International Search Report for Application No. PCT/EP2019/079605 dated Jan. 28, 2020.
Written Opinion of the International Searching Authority for Application No. PCT/EP2019/079605 dated Jan. 28, 2020.
Great Britain Search Report for Application No. 1817785.7 dated May 20, 2019.
T.P. Schultz, et al., Comparison of the Fungicidal Activities of (e)-4-Hydroxylated Stilbenes and Related Bibenzyls, Phytochemistry, pp. 2939-2945, vol. 30, No. 9, Pergamon Press, Great Britain (Jan. 1, 1991).
Thomas H. Fisher, et al., Fungicidal Activity of 3'-Substituted-3-Stilbenols, Holzforschung, 2001, pp. 568-572, vol. 55, Issue 6, Walter de Gruyter, Berlin (Nov. 6, 2001).
Jung-Yi Yu, et al., Selective cine Substitution of 1-Arylethenyl Acetates with Arylboron Reagents and a Diene/Rhodium Catalyst, Angewandte Chemie International Edition, 2010, pp. 6396-6399, vol. 49, No. 36, Wiley-VCH Verlag GmbH & Co. (Jul. 22, 2010).
Rachelle M. Arnold, et al., Direct Grafting of Poly(Pentafluorophenyl Acrylate) onto Oxides: Versatile Substrates for Reactive Microcapillary Printing and Self-Sorting Modification, Chemical Communications, Nov. 19, 2013, pp. 5307-5309, vol. 50, No. 40 (Jan. 1, 2014).
Masataka Nojima, et al., Structural Requirements for Pallidium Catalyst Transfer on a Carbon-Carbon Double Bond, Journal of the American Chemical Society, pp. 5682-5685, vol. 137, No. 17, ACS Publications (Apr. 28, 2015).
Paramita Bera, et al., Developmental variation in floral volatiles composition of a fragrant orchid *Zygopetalum maculatum* (Kunth) Garay, Natural Product Research, pp. 435-438, vol. 33, No. 3 (Mar. 18, 2019).

* cited by examiner

*Primary Examiner* — Jessica Whiteley
(74) *Attorney, Agent, or Firm* — Curatolo Sidoti & Trillis Co. ,LPA; Salvatore A. Sidoti; Floyd Trillis, III

(57) ABSTRACT

The present invention refers to alkoxybenzaldehyde derivatives and precursors thereof. The invention further refers to perfume compositions and fragranced article comprising them.

14 Claims, No Drawings

ALKOXYBENZALDEHYDE DERIVATIVES AND PRECURSORS THEREOF

CROSS REFERENCE TO RELATED APPLICATIONS

This application is a national stage application of International Application No. PCT/EP2019/079605, filed 30 Oct. 2019, which claims priority from Great Britain Patent Application No. 1817785.7, filed 31 Oct. 2018, both of which applications are incorporated herein by reference in their entireties.

This disclosure relates to alkoxybenzaldehyde derivatives possessing long lasting citrus odor characteristics. The invention furthermore refers to methods of their production, and to fragrance compositions containing these.

With constantly changing commercial and regulatory requirements, there is a constant search for new molecules that enhance fragrance notes or possess newly-available fragrance notes, in particular long lasting citrus-like odor notes.

Compounds possessing citrus-like odor notes are of particular interest, since they are associated by the consumer with freshness and/or cleanliness.

Alkoxybenzaldehydes, such as para-methoxy benzaldehyde (also known as anisic aldehyde), and their use as fragrance ingredients are known. They are described to possess very typical benzaldehyde-like odors, which are described in general as aromatic, anisic, with spicy gourmand nuances.

Whereas meta alkoxybenzaldehydes of formula (I) are reported in the literature, e.g. as intermediates for the preparation of pharmaceuticals, to the best of our knowledge, for none of them it has been reported or suggested any organoleptical properties, or any use as fragrance ingredient.

It has now surprisingly been found that meta alkoxybenzaldehydes of formula (I) as herein below defined do possess citrus-like odor profiles, essentially free of spicy gourmand side notes which would reduce the desired impression of freshness.

There is therefore provided in one aspect the use as fragrance of a compound of formula (I)

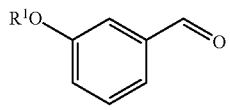

(I)

wherein $R^1$ is selected from linear or branched $C_3$-, $C_4$- and $C_5$-alkyl and $C_3$-, $C_4$- and $C_5$-alkenyl (e.g. butyl, pentyl, but-2-yl).

As a specific example of compounds of formula (I) one may cite, as non-limiting example, 3-butoxybenzaldehyde, which possesses a fresh citrus odor with a green nuance. This type of odor note combines particular well with other green and/or floral-aldehydic notes to create or improve an impression of cleanliness and/or freshness.

Further, non-limiting examples are compounds of formula (I) selected from
3-(sec-butoxy)benzaldehyde,
3-pentyloxybenzaldehyde,
3-((2-methylallyl)oxy)benzaldehyde, and
3-isopropoxybenzaldehyde.

The compounds of formula (I) may be added to a fragrance composition, that is, a formulation that combines individual fragrance ingredients to provide a desirable hedonic effect. These may be selected from any of the large range of such materials available to the art.

Typical, non-limiting examples of fragrance ingredients include
essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil and/or ylang-ylang oil;
alcohols, e.g. cinnamic alcohol ((E)-3-phenylprop-2-en-1-ol); cis-3-hexenol ((Z)-hex-3-en-1-ol); citronellol (3,7-dimethyloct-6-en-1-ol); dihydro myrcenol (2,6-dimethyloct-7-en-2-ol); Ebanol™ ((E)-3-methyl-5-(2,2,3-trimethylcyclopent-3-en-1-yl)pent-4-en-2-ol); eugenol (4-allyl-2-methoxyphenol); ethyl linalool ((E)-3,7-dimethylnona-1,6-dien-3-ol); farnesol ((2E,6Z)-3,7,11-trimethyldodeca-2,6,10-trien-1-ol); geraniol ((E)-3,7-dimethylocta-2,6-dien-1-ol); Super Muguet™ ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol™ (3,7-dimethyloct-6-en-1-ol); Sandalore™ (3-methyl-5-(2,2,3-trimethylcyclopent-3-en-1-yl)pentan-2-ol); terpineol (2-(4-methylcyclohex-3-en-1-yl)propan-2-ol); or Timberol™ (1-(2,2,6-trimethylcyclohexyl)hexan-3-ol); 2,4,7-trimethylocta-2,6-dien-1-ol, and/or [1-methyl-2(5-methylhex-4-en-2-yl)cyclopropyl]-methanol;
aldehydes and ketones, e.g. anisaldehyde (4-methoxybenzaldehyde); alpha amyl cinnamic aldehyde (2-benzylideneheptanal); Georgywood™ (1-(1,2,8,8-tetramethyl-1,2,3,4,5,6,7,8-octahydronaphthalen-2-yl) ethanone); Hydroxycitronellal (7-hydroxy-3,7-dimethyloctanal); Iso E Super® (1-(2,3,8,8-tetramethyl-1,2,3,4,5,6,7,8-octahydronaphthalen-2-yl) ethanone); Isoraldeine® ((E)-3-methyl-4-(2,6,6-trimethylcyclohex-2-en-1-yl)but-3-en-2-one); Hedione® (methyl 3-oxo-2-pentylcyclopentaneacetate); 3-(4-isobutyl-2-methylphenyl)propanal; maltol; methyl cedryl ketone; methylionone; verbenone; 2,6,10-trimethylundeca-5,9-dienal; 3-(4-ethylphenyl)-2,2-dimethylpropanal; 1-methyl-4-(4-methylpent-3-en-1-yl)cyclohex-3-ene-1-carbaldehyde; hex-2-enal and/or vanillin;
ether and acetals, e.g. Ambrox® (3a,6,6,9a-tetramethyl-2,4,5,5a,7,8,9,9b-octahydro-1H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); and/or Spirambrene® (2′,2′,3,7,7-pentamethylspiro[bicyclo [4.1.0]heptane-2,5′-[1,3]dioxane]);
esters and lactones, e.g. benzyl acetate; cedryl acetate ((1S,6R,8aR)-1,4,4,6-tetramethyloctahydro-1H-5,8a-methanoazulen-6-yl acetate); γ-decalactone (6-pentyltetrahydro-2H-pyran-2-one); Helvetolide® (2-(1-(3,3-dimethylcyclohexyl)ethoxy)-2-methylpropyl propionate); γ-undecalactone (5-heptyloxolan-2-one); and/or vetiveryl acetate ((4,8-dimethyl-2-propan-2-ylidene-3,3a,4,5,6,8a-hexahydro-1H-azulen-6-yl) acetate);

macrocycles, e.g. Ambrettolide ((Z)-oxacycloheptadec-10-en-2-one); ethylene brassylate (1,4-dioxacycloheptadecane-5,17-dione); and/or Exaltolide® (16-oxacyclohexadecan-1-one); and heterocycles, e.g. isobutylquinoline (2-isobutylquinoline).

The compounds of formula (I) may be employed into a fragrance application simply by directly mixing the compound as such or the fragrance composition comprising it with the fragrance application, and/or they may, in an earlier step, be entrapped with an entrapment material such as polymers, capsules, microcapsules and nanocapsules, liposomes, film formers, absorbents such as carbon or zeolites, cyclic oligosaccharides and mixtures thereof, and/or they may be chemically bonded to substrates, which are adapted to release the fragrance molecule upon application of an external stimulus such as light, air, moisture, elevated temperature, enzyme, or the like, and then mixed with the application.

While the compounds of formula (I) as hereinabove defined may not in themselves possess a particular strong odour, they combine usefully with other fragrance ingredients to provide useful fragrance profiles with long lasting citrus effects.

Thus, in one particular embodiment, the compounds of formula (I) may be added in the form of a precursor which is adapted to release two fragrance ingredients upon application of an external stimulus, one of which is a compound of formula (I).

In one particular embodiment the precursor has the general formula (II)

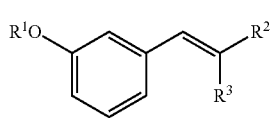

(II)

wherein $R^1$ has the same meaning as defined for formula (I), and $R^2$ is selected from the group consisting of $C_4$-$C_{14}$ alkyl, for example $C_5$-$C_{12}$ such as $C_8$, $C_9$, $C_{10}$ or alkyl;

$C_4$-$C_{14}$ alkyl, for example $C_5$-$C_{12}$ such as $C_8$, $C_9$, $C_{10}$ or alkyl, substituted with one —OH group and/or up to two (i.e. 0, 1 or 2) ether groups (e.g. $R^2$ is 6-methoxy-6-methyloctan-2-yl);

$C_4$-$C_{14}$ alkenyl, for example $C_5$-$C_{12}$ such as $C_8$, $C_9$, $C_{10}$ or alkenyl comprising, e.g. one or two carbon-to-carbon double bonds;

$C_4$-$C_{14}$ alkenyl substituted with one —OH group or an ether group, for example $C_5$-$C_{12}$ such as $C_8$, $C_9$, $C_{10}$ alkenyl substituted with one —OH group or an ether group comprising, e.g. one or two carbon-to-carbon double bonds (e.g. $R^2$ is (E)-8-hydroxy-4,8-dimethylnon-3-en-1-yl, or, pent-2-enyl);

$C_5$-$C_6$ cycloalkyl such as cyclohexyl, or cyclopentyl;

$C_5$-$C_8$ cycloalkyl (e.g. cyclohexyl, cyclopentyl) substituted with 1, 2, or 3 groups selected from $C_1$-$C_6$ alkyl (e.g. ethyl, isopropyl, tert-pentyl) and $C_2$-$C_4$ alkylidene (e.g. isopropenyl);

$C_5$-$C_8$ cycloalkenyl, e.g. $C_6$ cycloalkenyl such as cyclohexa-2,4-dienyl, cyclohex-1-enyl, cyclooct-3-enyl;

$C_5$-$C_8$ cycloalkenyl, such as cyclooct-3-enyl, wherein the cycloalkenyl-ring is substituted with 1, 2 or 3 groups selected from $C_1$-$C_4$ alkyl (e.g. ethyl, or isopropyl), $C_2$-$C_4$ alkylidene (e.g. isopropenyl), and $C_3$-$C_5$ cycloalkyl (e.g. $R^2$ is 7-methyl-spiro[4.5]dec-8-en-6-yl, spiro[4.5]dec-7-en-7-yl, 5,5-dimethylcyclohex-1-enyl, 2,6,6-trimethylcyclohex-1,3-dienyl, 2,4-dimethylcyclohex-3-enyl, or 4-isopropenyl(cyclohex-1en-1yl);

$(C_1$-$C_3)$alkyl$(C_5$-$C_6)$cycloalkyl wherein the cycloalkyl-ring is optionally substituted with one group selected from —OH group and =O group, and/or one or two ether group(s), and/or up to four $C_1$-$C_5$ alkyl groups (e.g. $R^2$ is (3-tertbutylcyclohexyl)ethyl, or (4-(1,1-dimethylpropyl)cyclohexyl)methyl, (3-oxo-2-pentylcyclopentyl)methyl);

$(C_1$-$C_4)$alkyl$(C_5$-$C_6)$cycloalkenyl wherein the cycloalkenyl-ring is optionally substituted with one —OH group, and/or one or two ether group(s), and/or up to four (i.e. 0, 1, 2, 3 or 4) $C_1$-$C_5$ alkyl groups (e.g. $R^2$ is (2,6,6-trimethylcyclohex-1-en-1-yl)ethyl, 1-(2,6,6-trimethylcyclohex-2-en-1-yl)butan-3-yl);

$(C_2$-$C_3)$alkenyl$(C_5$-$C_6)$cycloalkenyl wherein the cycloalkenyl-ring is optionally substituted with one —OH group, and/or one or two ether group(s), and/or up to four (i.e. 0, 1, 2, 3, or 4) $C_1$-$C_5$ alkyl groups (e.g. $R^2$ is (2,6,6-trimethylcyclohex-1-en-1-yl)ethenyl, (2,6,6-trimethylcyclohex-2-en-1-yl)ethenyl, (2,6,6-trimethylcyclohex-2-en-1-yl)prop-2-en-2-yl, (2,6,6-trimethylcyclohex-1-en-1-yl)prop-2-en-2-yl);

$C_6$-$C_{14}$ aryl, e.g. phenyl;

$C_6$-$C_{14}$ aryl wherein the aryl ring is substituted with up to 3 (i.e. 0, 1, 2, or 3) groups selected from $C_1$-$C_4$ alkyl (e.g. ethyl, iso-propyl, tert-butyl), —O—CH$_2$—O—, and —OR$^{11}$ wherein R$^{11}$ is independently selected from hydrogen and $C_1$-$C_4$ alkyl (e.g. ethyl, iso-propyl, tert-butyl);

$(C_1$-$C_4)$alkyl$(C_6$-$C_{14})$aryl, e.g. benzyl, 2-phenylethyl;

$(C_1$-$C_4)$alkyl$(C_6$-$C_{14})$aryl, such as benzyl or 2-phenylethyl wherein the aryl-ring is substituted with up to 2 groups (e.g. 1 group) selected from $C_1$-$C_4$ alkyl (e.g. ethyl, iso-propyl, tert-butyl), —O—CH$_2$—O—, and —OR$^{12}$ wherein R$^{12}$ is independently selected from hydrogen and $C_1$-$C_4$ alkyl (e.g. ethyl, iso-propyl, tert-butyl);

$(C_2$-$C_8)$alkenyl$(C_6$-$C_{14})$aryl, e.g. 2-phenylethylene-1-yl, 1-phenylhept-1-en-2-yl;

$(C_2$-$C_8)$alkenyl$(C_6$-$C_{14})$aryl wherein the aryl-ring is substituted with up to 2 groups (e.g. 1 group) selected from $C_1$-$C_4$ alkyl (e.g. ethyl, iso-propyl, tert-butyl), —O—CH$_2$—O—, and —OR$^{13}$ wherein R$^{13}$ is independently selected from hydrogen and $C_1$-$C_4$ alkyl (e.g. ethyl, iso-propyl, tert-butyl);

bi-, tri, or tetracyclic hydrocarbon ring comprising $C_8$-$C_{12}$ carbon atoms optionally substituted with up to 6 groups selected from $C_1$-$C_4$ alkyl (e.g. ethyl, iso-propyl, tert-butyl), —O—CH$_2$—O—, and —OR$^{14}$ wherein R$^{14}$ is independently selected from hydrogen and $C_1$-$C_4$ alkyl (e.g. ethyl, iso-propyl, tert-butyl), e.g. $R^2$ is 1,1,6,7-tetramethyl-1,2,3,4,5,6,7,8-octahydronaphthalen-7-yl, 2-((1,1-dimethyl-(2,3-dihydro-1H-indene))-6-yl)-eth-1-yl, 3,6,8,8-tetramethyl-2,3,4,7,8,8a-hexahydro-1H-3a,7-methanoazulen-5(4H)-ylidene, or 1,1,2,4,4,7-hexamethyl-1,2,3,4-tetrahydronaphthalene-6-yl;

$R^3$ is selected from hydrogen, $C_1$-$C_5$ alkyl, and $C_2$-$C_5$ alkenyl (e.g. but-3-enyl).

As used in relation to compounds of formula (II) unless otherwise indicated "alkyl" refers to straight chain or branched-chain hydrocarbon group; "alkenyl" refers to straight chain or branched-chain hydrocarbon group comprising at least one carbon-to-carbon double bond, e.g. 2 or 3 double bonds; "hydrocarbon ring" refers to saturated and unsaturated ring systems, preferably containing up to two carbon-to-carbon double bonds per ring, wherein the ring may be substituted with up to 3 (e.g. one or two) $C_1$-$C_3$ alkyl; and "ether group" refers to an oxygen atom connected to two carbon atoms.

In certain embodiments $R^3$ is hydrogen.

In particular embodiments $R^3$ is hydrogen and $R^2$ is selected from $C_4$-$C_{14}$ alkyl, for example $C_5$-$C_{12}$ such as $C_8$, $C_9$, $C_{10}$ or alkyl; $C_4$-$C_{14}$ alkenyl, for example $C_5$-$C_{12}$ such as $C_8$, $C_9$, $C_{10}$ or $C_{11}$ alkenyl comprising, e.g. one or two carbon-to-carbon double bonds; (E)-4,8-dimethylnon-3-en-8-ol-1-yl); and 6-methoxy-6-methyloctan-2-yl.

In other particular embodiments, $R^3$ is hydrogen and $R^2$ is $C_5$-$C_{12}$ alkenyl comprising one carbon-to-carbon double bond, e.g. $R^2$ is selected from Z-pent-2-en-1-yl, Z-oct-5en-1-yl, dodec-1-en-1-yl, non-3-en-1-yl (e.g. E-non-3-en-1-yl), dec-8-en-1-yl.

In further particular embodiments, $R^3$ is hydrogen and $R^2$ is $(C_1$-$C_4)$alkyl$(C_6)$aryl such as benzyl, 2-phenylethyl or 3-phenylpropyl wherein the aryl-ring is substituted with up to 2 groups (e.g. 1 group) selected from $C_1$-$C_4$ alkyl (e.g. ethyl, iso-propyl, tert-butyl, isobutyl), e.g., $R^2$ is

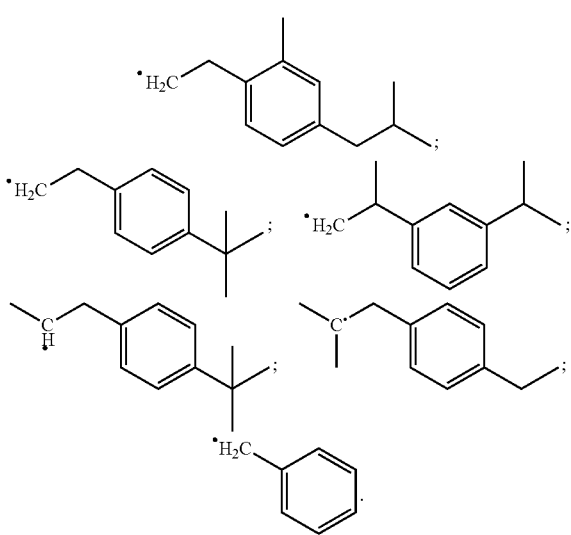

In further particular embodiments, $R^1$ is selected from butyl, pentyl, (1-methyl)propenyl, and 2-methylbut-2-enyl, $R^2$ is selected from $C_4$-$C_{14}$ alkyl, for example $C_6$-$C_{12}$ such as $C_8$, $C_9$, $C_{10}$ or $C_{11}$ alkyl; and $C_5$-$C_{14}$ alkenyl, for example $C_6$-$C_{12}$ such as $C_8$, $C_9$, $C_{10}$ or alkenyl comprising, e.g. one or two carbon-to-carbon double bonds, and $R^3$ is hydrogen.

In a further particular embodiment $R^2$ is pent-2-enyl (e.g. Z-pent-2-enyl) and $R^3$ is hydrogen.

The compounds of formula (II) act as precursors for the release, by spontaneous air oxidation, of an alkoxybenzaldehyde of formula (I) and a fragrant ketone or aldehyde of formula (III) ($R^2$—C(O)—$R^3$ wherein $R^2$ and $R^3$ have the same meaning as defined for the compounds of formula (II)).

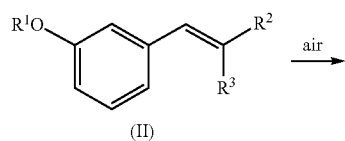

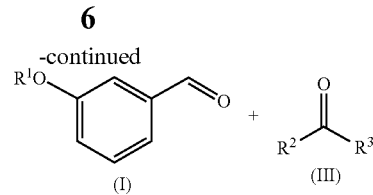

The compounds of formula (II) are very stable when not exposed to the ambient air, i.e. when stored as such, or in a diluent conventionally used in conjunction with odorants, such as dipropyleneglycol (DPG), isopropylmyristate (IPM), triethylcitrate (TEC), pentane-1,2-diol, and alcohol (e.g. ethanol), and known fragrance ingredients. Very good storage stability has been proven also when incorporated in consumer products such as detergent, shampoo and fabric conditioner. Thus the compounds of formula (II) may find use in a broad range of consumer products in which a prolonged and defined release of fragrant compounds is desired.

The concentration of oxygen in the air is sufficient for cleaving the compound of formula (II) in such a way, that the cleavage products can be detected in the ambient air, e.g. by olfaction or GC-MS analysis of headspace samples.

Compounds of formula (II) wherein $R^2$ is pent-2-enyl and $R^3$ is hydrogen releases, by spontaneous air oxidation, hex-3-enal (e.g., cis-3-hexenal), which is unstable as such, and thus not usable as such in perfumery.

As a specific example of precursors of compounds of formula (I) one may cite a compound of formula (II) wherein $R^1$ is $C_4$-$C_5$ alkyl (e.g. butyl), $R^2$ is hydrogen and $R^3$ is pent-2-en-1-yl (e.g. Z-pent-2-en-1yl) which gives rise to a precursor with particularly desirable properties, in that, in cleavage on exposure to air, it provides both a citrus note and a green note, a combination that is highly desirable in many commercial products, such as laundry detergents.

In a further particular embodiment the precursor of formula (II) are selected from
1-butoxy-3-((1E,4Z)-hepta-1,4-dien-1-yl)benzene;
1-butoxy-3-((1E,7Z)-deca-1,7-dien-1-yl)benzene;
1-(4-(3-butoxyphenyl)but-3-en-1-yl)-4-isobutyl-2-methylbenzene;
1-(4-(3-butoxyphenyl)but-3-en-1-yl)-2-isobutyl-4-methylbenzene;
1-(sec-butoxy)-3-((1E,4Z)-hepta-1,4-dien-1-yl)benzene;
1-((1E,4Z)-hepta-1,4-dien-1-yl)-3-(pentyloxy)benzene;
1-((1E,4Z)-hepta-1,4-dien-1-yl)-3-((2-methylallyl)oxy)benzene;
1-((1E,4Z)-hepta-1,4-dien-1-yl)-3-isopropoxybenzene;
1-butoxy-3-(4-(4-(tert-butyl)phenyl)but-1-en-1-yl)benzene;
1-butoxy-3-(4-(4-(tert-butyl)phenyl)-3-methylbut-1-en-1-yl)benzene;
1-butoxy-3-(4-(3-isopropylphenyl)pent-1-en-1-yl)benzene;
11-(3-butoxyphenyl)-2,6-dimethylundeca-6,10-dien-2-ol;
1-butoxy-3-(3-methyldodec-1-en-1-yl)benzene;
5-(4-(3-butoxyphenyl)-2-methylbut-3-en-1-yl)benzo[d][1,3]dioxole;
1-butoxy-3-(tetradeca-1,3-dien-1-yl)benzene;
1-butoxy-3-(3-phenylprop-1-en-1-yl)benzene;
1-butoxy-3-((5E)-undeca-1,5-dien-1-yl)benzene;
5-(5-(3-butoxyphenyl)pent-4-en-1-ylidene)octahydro-1H-4,7-methanoindene;
1-butoxy-3-(4-(4-ethylphenyl)-3,3-dimethylbut-1-en-1-yl)benzene;
1-butoxy-3-(7-methoxy-3,7-dimethylnon-1-en-1-yl)benzene; and
1-butoxy-3-(4-(4-isobutylphenyl)but-1-en-1-yl)benzene.

There is further provided a method of fragrancing a consumer product, comprising the addition to a consumer product base a compound of formula (I) or precursor thereof, e.g., a compound of formula (II).

The compounds according to formula (I) or its precursor, e.g., a compound of formula (II) may be used in a broad range of fragrance applications, e.g. in any field of fine and functional perfumery, such as perfumes, household products, laundry products, body care products and cosmetics.

The compounds of formula (I) or a precursor thereof (e.g., a compound of formula (II)) can be employed in widely varying amounts, depending upon the specific application and on the nature and quantity of other odorant ingredients. The proportion is typically from 0.0001 to 2 weight percent of the application. In one embodiment, the compounds may be employed in a fabric softener in an amount of from 0.0001 to 0.005 weight percent. In another embodiment, the compounds may be used in an alcoholic solution in amounts of from 0.01 to 3 weight percent, more particularly between 0.5 and 2 weight percent. However, these values are given only by way of example, since the experienced perfumer may also achieve effects or may create novel accords with lower or higher concentrations, e.g. up to about 20 weight percent based on the fragrance composition.

The compounds of formula (I) or a precursor thereof (e.g. a compound of formula (II)) may be employed in a consumer product base simply by directly mixing the compound of formula (I) or a precursor thereof (e.g. a compound of formula (II)), or a fragrance composition comprising a compound of formula (I) or a precursor thereof (e.g. a compound of formula (II)) with the consumer product base, or it may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, and then mixed with the consumer product base.

Thus, the invention additionally provides a method of manufacturing a fragranced article, comprising the incorporation of a compound of formula (I) or a precursor thereof (e.g. a compound of formula (II)), as a fragrance ingredient, either by directly admixing it to the consumer product base or by admixing a fragrance composition comprising the compound of formula (I) or a precursor thereof (e.g. a compound of formula (II)), which may then be mixed with a consumer product base, using conventional techniques and methods. Through the addition of an olfactory acceptable amount of the compound of formula (I) or a precursor thereof (e.g. a compound of formula (II)) the odor notes of a consumer product base will be improved, enhanced, or modified.

Thus, the invention furthermore provides a method for improving, enhancing or modifying a consumer product base by means of the addition thereto of an olfactorily acceptable amount of the compound of formula (I) or a precursor thereof (e.g. a compound of formula (II)).

The invention also provides a fragranced article comprising:
a) as odorant the compound of formula (I),a mixture thereof, or a precursor thereof (e.g. a compound of formula (II)); and
b) a consumer product base.

As used herein, 'consumer product base' means a composition for use as a consumer product to fulfill specific actions, such as cleaning, softening, and caring or the like.

Examples of such products include fine perfumery, e.g. perfume and eau de toilette; fabric care, household products and personal care products such as cosmetics, laundry care detergents, rinse conditioner, personal cleansing composition, detergent for dishwasher, surface cleaner; laundry products, e.g. softener, bleach, detergent; body-care products, e.g. shampoo, shower gel; air care products (includes products that contain preferably volatile and usually pleasant-smelling compounds which advantageously can even in very small amounts mask unpleasant odors). Air fresheners for living areas contain, in particular, natural and synthetic essential oils such as pine needle oils, citrus oil, eucalyptus oil, lavender oil, and the like, in amounts for example of up to 50% by weight. As aerosols they tend to contain smaller amounts of such essential oils, by way of example less than 5% or less than 2% by weight, but additionally include compounds such as acetaldehyde (in particular, <0.5% by weight), isopropyl alcohol (in particular, <5% by weight), mineral oil (in particular, <5% by weight), and propellants.

In one particular embodiment the consumer product base (e.g. bleach products) are essentially free of aromatic imides.

This list of products is given by way of illustration, and is not to be regarded as being in any way limiting.

The compounds of formula (I) may be prepared by etherification reaction of 3-hydroxy benzaldehyde with an alkyl halide $R^1$—X, X being a chloride, bromide, iodide or a toluenesulfonate, in a suitable solvent, such as tetrahydrofurane or dimethyl formamide, and in the presence of a base, such as potassium or sodium carbonate or hydroxide.

Other conditions for the formation of phenyl ethers can be employed which are known to the person skilled in the art of organic synthesis.

The compounds of formula (II) may be prepared by a Grignard reaction between—$R^2R^3$CHMgBr and an alkoxybenzaldehyde of formula (I) in a solvent like tetrahydrofurane or diethyl ether, followed by standard workup under conditions known to the person skilled in the art and dehydration of the resulting secondary benzyl alcohol in the presence of a catalyst, e.g. p-toluene sulfonic acid. Other double bond forming reactions might be employed, such as the Wittig reaction.

The disclosure is further described with reference to the following non-limiting examples, which depict particular embodiments.

EXAMPLE 1

3-butoxybenzaldehyde and a Precursor Thereof 1.1: 3-butoxybenzaldehyde

A solution of 3-hydroxybenzaldehyde (20 g, 164 mmol, 1.0 equiv.) in DMF (100 mL) was treated with potassium carbonate (27.2 g, 197 mmol, 1.2 equiv.). The resulting mixture was heated to 80° C. and then slowly treated with 1-bromobutane (21.2 ml, 197 mmol, 1.2 eq.). The mixture was stirred at 80° C. for 1 h then cooled to 25° C., filtered to remove solids, diluted with MTBE (500 mL) and washed with water (3×100 mL). The organic layer was dried over $MgSO_4$, filtered and concentrated. The resulting oil was vacuum-distilled over a 5 cm Vigreux column, collecting at 135-137° C. at 25 mbar to give 3-butoxybenzaldehyde (25.3 g, 142 mmol, 87%) as a clear, colorless liquid.

$^1$H NMR ($CDCl_3$, 400 MHz): δ=9.99 (s, 1H), 7.44-7.47 (m, 2H), 7.39-7.42 (m, 1H), 7.17-7.21 (m, 1H), 4.04 (t, J=6.5 Hz, 2H), 1.76-1.85 (m, 2H), 1.46-1.58 (m, 2H), 1.00 ppm (t, J=7.3 Hz, 3H).

$^{13}$C NMR ($CDCl_3$, 101 MHz): δ=192.3, 159.7, 137.8, 130.0, 123.3, 122.0, 112.8, 68.0, 31.2, 19.2, 13.8 ppm.

MS (EI, 70 eV): 178 (30, [M]+•), 123 (11), 122 (100), 121 (100), 77 (9), 65 (13), 41 (18), 39 (12), 29 (22), 27 (9).

Odor description (10% solution in DPG on paper blotter, 24 h): fresh citrus, citral, lemongrass, verbena, green, slightly hot iron, slightly fatty.

1.2: 1-butoxy-3-((1E,4Z)-hepta-1,4-dien-1-yl)benzene

In a flask flushed with nitrogen were placed magnesium turnings (0.750 g, 31 mmol, 1.3 equiv.) and THF (2 mL). (Z)-1-chlorohex-3-ene (3.66 g, 31 mmol, 1.3 equiv.) in THF (60 mL) was added dropwise at reflux, the reaction mixture further heated to reflux for 12 h and then cooled to 0° C. 3-Butoxybenzaldehyde (4.00 g, 22 mmol, 1.0 equiv.) was added, the reaction mixture was stirred at 25° C. for 30 min and poured on ice-cold 1 M aq. HCl-solution (100 mL). The aqueous layer was extracted with MTBE (2×50 mL). The combined organic phases were washed with brine (50 mL), dried over $MgSO_4$, filtered and concentrated. The resulting oil was dissolved in Toluene (50 mL), treated at 25° C. with p-Toluenesulfonic acid monohydrate (0.21 g, 1.12 mmol, 0.05 equiv.) and heated to reflux on a Dean-Stark apparatus for 3 h. The resulting mixture was cooled to 25° C., diluted with MTBE (100 mL), washed with saturated aqueous $NaHCO_3$ solution (50 mL), brine (50 mL), the organic layer was dried over $MgSO_4$, filtered and concentrated. The resulting crude material was purified by flash column chromatography eluting with a gradient of 1-7% MTBE in Hexanes to give 1-butoxy-3-((1E,4Z)-hepta-1,4-dien-1-yl) benzene (2.06 g, 8.43 mmol, 37.6%) as a clear, colorless liquid.

$^1$H-NMR ($CDCl_3$, 400 MHz): δ=7.22 (dd, J=8.2, 7.6 Hz, 1H), 6.90-6.98 (m, 2H), 6.77 (ddd, J=8.2, 2.6, 0.7 Hz, 1H), 6.39 (dt, J=15.9, 1.5 Hz, 1H), 6.22 (dt, J=15.9, 6.4 Hz, 1H), 5.39-5.58 (m, 2H), 3.99 (t, J=6.5 Hz, 2H), 2.94-3.01 (m, 2H), 2.08-2.18 (m, 2H), 1.75-1.84 (m, 2H), 1.46-1.56 (m, 2H), 1.02 (t, J=7.6 Hz, 6H), 1.00 ppm (t, J=7.6 Hz, 3H).

$^{13}$C-NMR ($CDCl_3$, 101 MHz): δ=159.4, 139.2, 133.0, 129.9, 129.4, 129.3, 126.0, 118.5, 113.1, 111.9, 67.6, 31.4, 30.6, 20.6, 19.3, 14.3, 13.9 ppm MS (EI, 70 eV): 244 (34, [M]+•), 159 (49), 145 (100), 133 (16), 131 (24), 128 (18), 120 (39), 115 (27), 41 (20), 29 (21).

Odour description (1% solution in EtOH on paper blotter, 24 h): green, citrus, apple, lime, crushed leaves

1.3: 1-butoxy-3-((1E,7Z)-deca-1,7-dien-1-yl)benzene

The procedure described in Example 1.2. was repeated with the Grignard reagent derived from Z-9-bromonon-3-ene (13.8 g, 67 mmol, 1.2 equiv.) and magnesium (1.64 g, 67 mmol, 1.2 equiv.) in THF (150 mL) and 3-butoxybenzaldehyde (Example 1.1), followed by dehydration of the crude product with p-toluene sulfonic acid (500 mg) in toluene (100 mL). The crude product was purified by flash chromatography on silica gel with a gradient heptane 100% to heptane/MTBE 50:1 to yield (2.18 g, 28%) as a slightly yellow liquid.

$^1$H-NMR ($CDCl_3$, 400 MHz): δ=7.18 (t, J=7.9 Hz, 1H), 6.86-6.94 (m, 2H), 6.73 (ddd, J=8.2, 2.4, 0.7 Hz, 1H), 6.29-6.37 (m, 1H), 6.14-6.26 (m, 1H), 5.28-5.48 (m, 2H), 3.96 (t, J=6.5 Hz, 2H), 2.15-2.25 (m, 2H), 1.94-2.10 (m, 4H), 1.72-1.82 (m, 2H), 1.33-1.57 (m, 6H), 0.96 (td, J=7.5, 6.4 Hz, 6H).

$^{13}$C-NMR ($CDCl_3$, 101 MHz): δ=159.4 (s), 139.4 (s), 131.8 (s), 131.3 (s), 129.8 (s), 129.4 (s), 129.0 (s), 118.5 (s), 113.0 (s), 112.9-113.0 (m), 111.9 (s), 67.6 (s), 32.9 (s), 31.4 (s), 29.3 (s), 29.0 (s), 27.0 (s), 20.5 (s), 19.3 (s), 14.4 (s), 13.9 (s).

MS (EI, 70 eV): 286(16), 257(13), 230(6), 176(18), 164(46), 145(69), 127(100), 108(58), 107(58), 55(54), 41(92), 29(50).

Odour description (1% solution in EtOH on paper blotter, 24 h): melon, green, citrus, floral.

1.4: 1-(4-(3-butoxyphenyl)but-3-en-1-yl)-4-isobutyl-2-methylbenzene and 1-(4-(3-butoxyphenyl)but-3-en-1-yl)-2-isobutyl-4-methylbenzene

A) (3-butoxyphenyl)methanol

3-Butoxybenzaldehyde (18.5 g, 104 mmol, 1.0 equiv.) in THF (80 mL) was added dropwise to a suspension of $LiAlH_4$ (1.26 g, 31.5 mmol, 0.304 eq.) in THF (120 mL) at 25° C. After 1 h, the mixture was cooled to 0° C. and treated carefully with water (1.25 mL) followed by 15% aq. NaOH (1.25 mL) and finally water (3.75 mL). The mixture was warmed to 40° C. and treated with $MgSO_4$ then filtered. The filtrate was concentrated to give (3-butoxyphenyl)methanol (17.3 g, 96 mmol, 92%) as a pale yellow oil.

$^1$H-NMR ($CDCl_3$, 400 MHz): δ=7.23-7.30 (m, 1H), 6.89-6.95 (m, 2H), 6.82-6.87 (m, 1H), 4.62 (s, 2H), 3.98 (t, J=6.6 Hz, 2H), 2.64 (br s, 1H), 1.74-1.84 (m, 2H), 1.46-1.59 (m, 2H), 1.02 ppm (t, J=7.3 Hz, 3H).

$^{13}$C-NMR ($CDCl_3$, 101 MHz): δ=159.4, 142.6, 129.5, 118.9, 113.7, 112.9, 67.7, 65.1, 31.4, 19.3, 13.9 ppm.

MS (EI, 70 eV): 180 (52, [M]$^{+*}$), 124 (100), 123 (39), 107 (19), 106 (37), 105 (25), 95 (50), 78 (18), 77 (20), 41 (13).

B) 1-(4-(3-butoxyphenyl)but-3-en-1-yl)-4-isobutyl-2-methylbenzene and 1-(4-(3-butoxyphenyl)but-3-en-1-yl)-2-isobutyl-4-methylbenzene (3-butoxyphenyl)methanol (17.0 g, 94 mmol, 1.0 equiv.) was combined with triphenylphosphine hydrobromide (32.4 g, 94 mmol, 1.0 equiv.) and acetonitrile (100 mL) and the resulting mixture heated to reflux under nitrogen atmosphere for 20 h. The resulting mixture was concentrated then suspended in $Et_2O$ (70 mL) and placed in the fridge (4° C.) for 5 h. The precipitated solid was filtered and washed with $Et_2O$ (2×50 mL) and then dried under high vacuum at 25° C. for 2 h. The resulting solid was suspended in THF (350 mL), cooled to 5° C. and treated portion-wise with KOtBu (10.38 g, 92 mmol, 0.98 equiv.), maintaining the temperature between 0-5° C. The resulting bright red mixture was stirred for 20 min at 5° C. then treated dropwise over 40 min with a solution of 3-(4-isobutyl-2-methylphenyl)propanal (16.1 g, 78 mmol, 0.83 equiv.) and 3-(2-isobutyl-4-methylphenyl) propanal (2.84 g, 14 mmol, 0.15 equiv.) in THF (50 mL). The resulting mixture was allowed to warm to 25° C. and stirred for 2 h. The mixture was then poured onto a mixture of acetic acid (20 mL) and ice-water (500 mL), extracted with heptane (2×200 mL), the extracts washed successively with 70% methanol (3×100 mL), sat. aq. $KHCO_3$ (2×100 mL), water (2×100 mL), dried over $MgSO_4$, filtered and evaporated. The resulting crude material was purified by flash column chromatography eluting with a gradient of 1-7% MTBE in Hexanes to give an isomeric mixture of 1-(4-(3-butoxyphenyl)but-3-en-1-yl)-4-isobutyl-2-methylbenzene and 1-(4-(3-butoxyphenyl)but-3-en-1-yl)-2-isobutyl-4-methylbenzene (22.3 g, 63.6 mmol, 68%) as a clear, pale green liquid (isomers 1 to 4 obtained in ratio 3:25:9:63 (GC) (isomer 1:isomer 2:isomer 3:isomer 4))

¹H NMR (CHLOROFORM-d, 400 MHz): δ=7.11-7.23 (m), 7.01-7.09 (m), 6.86-6.98 (m), 6.67-6.84 (m), 6.34-6.44 (m), 6.21-6.33 (m), 5.66-5.75 (m), 3.89-3.99 (m), 2.67-2.77 (m), 2.54-2.64 (m), 2.36-2.50 (m), 2.31 (s), 2.30 (s), 2.28 (s), 2.25 (s), 1.69-1.90 (m), 1.42-1.56 (m), 0.86-1.01 ppm (m)

¹³C NMR (BENZENE-d₆, 101 MHz): δ=159.7, 159.7, 159.5, 159.4, 139.3, 139.4, 139.3, 139.3, 139.1, 139.1, 139.0, 139.0, 137.1, 136.9, 136.6, 136.5, 135.3, 135.2, 134.8, 134.8, 132.1, 131.0, 131.0, 130.9, 130.9, 130.5, 130.5, 130.1, 129.6, 129.4, 129.2, 129.2, 129.1, 129.1, 128.7, 128.7, 128.7, 128.7, 126.8, 126.8, 126.7, 126.7, 121.3, 121.1, 118.6, 115.4, 115.1, 115.0, 113.2, 113.1, 112.8, 112.8, 112.3, 111.5, 67.1, 67.1, 67.1, 67.0, 45.0, 41.9, 41.9, 34.9, 33.8, 33.0, 32.8, 32.4, 32.2, 31.3, 31.3, 30.4, 30.2, 30.2, 30.1, 29.9, 29.8, 29.3, 22.4, 22.4, 22.2, 21.2, 20.8, 20.8, 19.2, 19.2, 19.1, 19.1, 13.6, 13.6 ppm.

MS (EI, 70 eV) (Isomer 1): 350 (12, [M]⁺˙), 189 (9), 161 (58), 133 (29), 120 (10), 119 (100), 117 (9), 115 (9), 105 (17), 55 (15).

MS (EI, 70 eV) (Isomer 2): 350 (8, [M]⁺˙), 189 (6), 162 (13), 161 (100), 133 (19), 119 (25), 118 (9), 117 (5), 115 (6), 105 (11).

MS (EI, 70 eV) (Isomer 3): 350 (11, [M]⁺˙), 189 (10), 162 (8), 161 (62), 133 (35), 120 (10), 119 (100), 115 (8), 105 (18), 55 (16).

MS (EI, 70 eV) (Isomer 4): 350 (9, [M]⁺˙), 189 (8), 162 (13), 161 (100), 133 (23), 119 (25), 118 (9), 115 (6), 105 (11), 43 (5).

Odour description (1% solution in EtOH on paper blotter, 24 h): citrus, aldehydic, muguet, slightly fatty.

EXAMPLE 2

3-(sec-butoxy)benzaldehyde and a Precursor Thereof 2.1: 3-(sec-butoxy)benzaldehyde The procedure described in Example 1.1. was repeated with 3-hydroxybenzaldehyde (6.0 g, 49.1 mmol, 1 equiv.), potassium carbonate (13.6 g, 98 mmol, 2 equiv.) and 2-bromobutane (10.1 g, 73.7 mmol, 1.5 equiv.) in DMF (60 mL). The crude product was purified by flash chromatography on silica gel with hexane/MTBE 93:7 followed by vacuum bulb-to-bulb distillation at 114° C./0.03 mbar to yield 3-(sec-butoxy)benzaldehyde (6.8 g, 77%) as a colorless liquid.

¹H-NMR (CDCl₃, 400 MHz): δ=9.80-10.16 (m, 1H), 7.42-7.46 (m, 2H), 7.38-7.41 (m, 1H), 7.14-7.20 (m, 1H), 4.40 (sxt, J=6.0 Hz, 1H), 1.61-1.84 (m, 2H), 1.33 (d, J=5.9 Hz, 3H), 1.00 (t, J=7.5 Hz, 3H).

¹³C-NMR (CDCl₃, 101 MHz): δ 192.2 (d), 158.8 (s), 137.8 (s), 130.1 (d), 123.1 (d), 123.0 (d), 114.2 (d), 75.3 (d), 29.1 (t), 19.1 (q), 9.7 (q).

MS (EI, 70 eV): 178 (15, M+), 122 (100), 121 (95), 93 (8), 77 (7), 65 (11), 57 (7), 41 (9), 29 (18).

Odour description (10% solution in DPG on paper blotter, 4 h): citrus, fruity, phenolic.

2.2: 1-(sec-butoxy)-3-((1E,4Z)-hepta-1,4-dien-1-yl)benzene

The procedure described in Example 1.2. was repeated with (Z)-hex-3-en-1-ylmagnesium chloride (0.65 M in THF, 26 mL, 16.9 mmol, 1.2 equiv.) and 3-(sec-butoxy)benzaldehyde (2.5 g, 14.3 mmol, 1 equiv.) in THF (50 mL), followed by dehydration of the crude product with p-toluene sulfonic acid (286 mg, 1.5 mmol, 0.1 equiv.) in toluene (100 mL). The crude product was purified by flash chromatography on silica gel with hexane/MTBE 100:1 to yield 1-(sec-butoxy)-3-((1E,4Z)-hepta-1,4-dien-1-yl)benzene (1.43 g, 39%) as a colorless liquid.

¹H-NMR (CDCl₃, 400 MHz): δ=7.22 (t, J=7.8 Hz, 1H), 6.91-6.98 (m, 2H), 6.78 (ddd, J=8.1, 2.5, 0.9 Hz, 1H), 6.36-6.44 (m, 1H), 6.18-6.27 (m, 1H), 5.41-5.59 (m, 2H), 4.34 (sxt, J=6.1 Hz, 1H), 2.99 (br. t, J=6.7 Hz, 2H), 2.14 (quind, J=7.4, 1.2 Hz, 2H), 1.60-1.85 (m, 2H), 1.33 (d, J=6.1 Hz, 3H), 1.03 (q, J=7.6 Hz, 3H), 1.00 (q, J=7.3 Hz, 3H).

¹³C-NMR (CDCl₃, 101 MHz): δ 158.4 (s), 139.3 (s), 133.0 (d), 129.9 (d), 129.4 (d), 129.2 (d), 126.0 (d), 118.5 (d), 114.4 (d), 113.6 (d), 75.0 (d), 30.6 (t), 29.3 (t), 20.6 (t), 19.3 (q), 14.3 (q), 9.8 (q).

MS (EI, 70 eV): 244 (16, M⁺), 159 (62), 146 (17), 145 (100), 131 (22), 120 (56), 115 (27), 81 (19), 41 (18), 29 (16).

Odour description (1% solution in EtOH on paper blotter, 24 h): green, citrus, crushed leaves

EXAMPLE 3

3-Pentyloxybenzaldehyde and Precursor Thereof 3.1: 3-Pentyloxybenzaldehyde

The procedure described in Example 1.1. was repeated with 3-hydroxybenzaldehyde (6.0 g, 49.1 mmol, 1 equiv.), potassium carbonate (13.6 g, 98 mmol, 2 equiv.) and 1-bromopentane (8.9 g, 59.0 mmol, 1.2 equiv.) in DMF (60 mL). The crude product was purified by flash chromatography on silica gel with hexane/MTBE 93:7 followed by vacuum bulb-to-bulb distillation at 130° C./0.03 mbar to yield 3-Pentyloxybenzaldehyde (8.0 g, 84%) as a colorless liquid.

¹H-NMR (CDCl₃, 400 MHz): δ 9.98 (s, 1H), 7.43-7.47 (m, 2H), 7.38-7.42 (m, 1H), 7.15-7.22 (m, 1H), 4.03 (t, J=6.6 Hz, 2H), 1.78-1.88 (m, 2H), 1.35-1.52 (m, 4H), 0.96 (t, J=7.3 Hz, 3H).

¹³C-NMR (CDCl₃, 101 MHz): δ 192.2 (d), 159.7 (s), 137.8 (s), 130.0 (d), 123.3 (d), 121.9 (d), 112.8 (d), 68.3 (t), 28.8 (t), 28.2 (t), 22.4 (t), 14.0 (d).

MS (EI, 70 eV): 192 (21, M+), 122 (100), 121 (78), 105 (5), 93 (6), 77 (9), 71 (3), 70 (8), 65 (9), 55 (10), 43 (30), 29 (23).

Odour description (10% solution in DPG on paper blotter, 4 h): floral, watery, citrus, fatty.

3.2: 1-((1E,4Z)-hepta-1,4-dien-1-yl-3-(pentyloxy) benzene

The procedure described in Example 1.2. was repeated with (Z)-hex-3-en-1-ylmagnesium chloride (0.65 M in THF, 38.4 mL, 25.0 mmol, 1.2 equiv.) and 3-(pentyloxy)benzaldehyde (4.0 g, 20.8 mmol, 1 equiv.) in THF (50 mL), followed by dehydration of the crude product with p-toluene sulfonic acid (432 mg, 2.3 mmol, 0.1 equiv.) in toluene (100 mL). The crude product was purified by flash chromatography on silica gel with hexane/MTBE 100:1 to yield 1-((1E,4Z)-hepta-1,4-dien-1-yl)-3-(pentyloxy)benzene (2.84 g, 47%) as a colorless liquid.

¹H-NMR (CDCl₃, 400 MHz): δ 7.18-7.32 (m, 1H), 6.87-7.00 (m, 2H), 6.78 (ddd, J=8.2, 2.4, 0.9 Hz, 1H), 6.34-6.47 (m, 1H), 6.16-6.29 (m, 1H), 5.40-5.61 (m, 2H), 3.99 (t, J=6.6 Hz, 2H), 2.99 (br. t, J=6.7 Hz, 2H), 2.10-2.20 (m, 2H), 1.77-1.87 (m, 2H), 1.37-1.54 (m, 4H), 1.04 (t, J=7.6 Hz, 3H), 0.98 (t, J=7.1 Hz, 3H).

$^{13}$C-NMR (CDCl$_3$, 101 MHz): δ 159.4 (s), 139.2 (s), 133.0 (d), 129.9 (d), 129.4 (d), 129.3 (d), 126.0 (d), 118.5 (d), 113.1 (d), 112.0 (d), 67.9 (t), 30.6 (t), 29.1 (t), 28.3 (t), 22.5 (t), 20.6 (t), 14.3 (q), 14.1 (q).

MS (EI, 70 eV): 258(21, M$^+$), 159(48), 145(100), 133 (18), 131(22), 128(18), 120(41), 115(27), 43(25), 41(20).

Odour (1% solution in EtOH on paper blotter, 24 h): green, citrus, geranium leaves

EXAMPLE 4

3-((2-methylallyl)oxy)benzaldehyde and Precursor Thereof

4.1: 3-((2-methylallyl)oxy)benzaldehyde

The procedure described in Example 1.1. was repeated with 3-hydroxybenzaldehyde (5.0 g, 40.9 mmol, 1 equiv.), potassium carbonate (11.3 g, 82 mmol, 2 equiv.) and 3-Bromo-2-methylpropene (6.63 g, 49.1 mmol, 1.2 equiv.) in DMF (60 mL). The crude product was purified by flash chromatography on silica gel with hexane/MTBE 93:7 followed by vacuum bulb-to-bulb distillation at 129° C./0.03 mbar to yield 3-((2-methylallyl)oxy)benzaldehyde (5.2 g, 72%) as a colorless liquid.

$^1$H-NMR (CDCl$_3$, 400 MHz): δ 9.98 (s, 1H), 7.40-7.50 (m, 3H), 7.21 (dt, J=7.0, 2.5 Hz, 1H), 5.10-5.15 (m, 1H), 5.02 (td, J=2.1, 1.0 Hz, 1H), 4.50 (s, 2H), 1.85 (br. d, J=0.7 Hz, 3H).

$^{13}$C-NMR (CDCl$_3$, 101 MHz): δ 192.1 (d), 159.3 (s), 140.3 (s), 137.8 (s), 130.0 (d), 123.5 (d), 122.0 (d), 113.3 (d), 113.1 (t), 71.9 (t), 19.4 (q).

MS (EI, 70 eV): 176 (11, M+), 161 (31), 158 (8), 147 (11), 133 (10), 121 (18), 105 (5), 92 (5), 77 (8), 65 (12), 55 (100), 39 (33), 29 (29).

Odour description (10% solution in DPG on paper blotter, 4 h): fresh, floral, citrus, anisic.

4.2: 1-((1E,4Z)-hepta-1,4-dien-1-yl)-3-((2-methylallyl)oxy)benzene

The procedure described in Example 1.2. was repeated with (Z)-hex-3-en-1-ylmagnesium chloride (0.65 M in THF, 52.4 mL, 25.0 mmol, 1.2 equiv.) and 3-((2-methylallyl)oxy) benzaldehyde (5.0 g, 28.4 mmol, 1 equiv.) in THF (50 mL), followed by dehydration of the crude product with p-toluene sulfonic acid (584 mg, 2.3 mmol, 0.1 equiv.) in toluene (100 mL). The crude product was purified by flash chromatography on silica gel with hexane/MTBE 100:1 to yield 1-((1E,4Z)-hepta-1,4-dien-1-yl)-3-((2-methylallyl)oxy)benzene (1.49 g, 20%) as a colorless liquid.

$^1$H-NMR (CDCl$_3$, 400 MHz): δ 7.23 (t, J=7.8 Hz, 1H), 6.94-7.02 (m, 2H), 6.81 (ddd, J=8.3, 2.5, 1.0 Hz, 1H), 6.41 (dt, J=15.9, 1.5 Hz, 1H), 6.24 (dt, J=15.7, 6.6 Hz, 1H), 5.41-5.61 (m, 2H), 5.12-5.18 (m, 1H), 4.98-5.06 (m, 1H), 4.48 (br. s, 2H), 3.00 (t, J=6.7 Hz, 2H), 2.09-2.22 (m, 2H), 1.88 (br. s, 3H), 1.04 (t, J=7.6 Hz, 3H).

$^{13}$C-NMR (CDCl$_3$, 101 MHz): δ 159.0 (s), 141.0 (s), 139.2 (s), 133.1 (d), 129.8 (d), 129.4 (d), 129.4 (s), 126.0 (d), 118.8 (d), 113.4 (d), 112.7 (t), 112.3 (d), 71.7 (t), 30.6 (t), 20.6 (t), 19.5 (q), 14.3 (q).

MS (EI, 70 eV): 242(15, M$^+$), 174(15), 159(32), 145(61), 131(44), 129(43), 128(42), 117(41), 115(60), 91(33), 55(100), 29(35).

Odour description (1% solution in EtOH on paper blotter, 24 h): green, citrus, anisic, floral.

EXAMPLE 5

3-isopropoxybenzaldehyde and Precursor Thereof

5.1: 3-isopropoxybenzaldehyde

The procedure described in Example 1.1. was repeated with 3-hydroxybenzaldehyde (6.0 g, 49.1 mmol, 1 equiv.), potassium carbonate (13.6 g, 98 mmol, 2 equiv.) and 2-bromopropane (7.25 g, 59 mmol, 1.2 equiv.) in DMF (60 mL). The crude product was purified by flash chromatography on silica gel with hexane/MTBE 93:7 followed by vacuum bulb-to-bulb distillation at 120° C./0.03 mbar to yield 3-isopropoxybenzaldehyde (5.88 g, 73%) as a colorless liquid.

$^1$H-NMR (CDCl$_3$, 400 MHz): δ=9.98 (s, 1H), 7.38-7.46 (m, 3H), 7.13-7.19 (m, 1H), 4.64 (spt, J=6.1 Hz, 1H), 1.37 (d, J=6.1 Hz, 6H).

$^{13}$C-NMR (CDCl$_3$, 101 MHz): δ=192.2 (d), 158.5 (s), 137.8 (s), 130.1 (d), 123.1 (d), 123.0 (d), 114.2 (d), 70.2 (d), 21.9 (2q).

MS (EI, 70 eV): 164 (13, M+), 122 (73), 121 (100), 93 (9), 77 (4), 65 (11), 43 (11), 39 (13), 27 (7).

Odour description (10% solution in DPG on paper blotter, 4 h): green, phenolic, citrus, medicinal.

5.2: 1-((1E,4Z)-hepta-1,4-dien-1-yl)-3-isopropoxybenzene

The procedure described in Example 1.2. was repeated with (Z)-hex-3-en-1-ylmagnesium chloride (1.3 M in THF, 29 mL, 37.5 mmol, 1.5 equiv.) and 3-isopropoxybenzaldehyde (4.0 g, 24.4 mmol, 1 equiv.) in THF (50 mL), followed by dehydration of the crude product with p-toluene sulfonic acid (432 mg, 2.3 mmol, 0.1 equiv.) in toluene (100 mL). The crude product was purified by flash chromatography on silica gel with hexane/MTBE 100:1 to yield 1-((1E,4Z)-hepta-1,4-dien-1-yl)-3-isopropoxybenzene (1.54 g, 29%) as a colorless liquid.

$^1$H-NMR (CDCl$_3$, 400 MHz): δ=7.22 (t, J=7.8, 1H), 6.90-6.98 (m, 2H), 6.78 (ddd, J=8.1, 2.5, 0.9 Hz, 1H), 6.39 (dt, J=15.7, 1.2, 1H), 6.22 (dt, J=15.9, 6.6 Hz, 1H), 5.42-5.59 (m, 2H), 4.59 (spt, J=5.6 Hz, 1H), 2.99 (br. t, J=6.8 Hz, 2H), 2.10-2.20 (m, 2H), 1.37 (d, J=5.9 Hz, 6H), 1.04 (t, J=7.6 Hz, 3H).

$^{13}$C-NMR (CDCl$_3$, 101 MHz): δ=158.1 (s), 139.3 (s), 133.0 (d), 129.9 (d), 129.4 (d), 129.3 (d), 126.0 (d), 118.6 (d), 114.4 (d), 113.6 (d), 69.8 (d), 30.6 (t), 22.1 (2q), 20.6 (t), 14.3 (q).

MS (EI, 70 eV): 230(18), 159(60), 145(100), 131(26), 120(54), 115(29), 107(18), 81(20), 43(21), 41(19).

Odour description (1% solution in EtOH on paper blotter, 24 h): green, citrus, metallic, fatty.

EXAMPLE 6a-6m

6a: 1-butoxy-3-(4-(4-(tert-butyl)phenyl)but-1-en-1-yl)benzene

The procedure described in example 1.4 can be repeated by replacing the solution of 3-(4-isobutyl-2-methylphenyl) propanal and 3-(2-isobutyl-4-methylphenyl)propanal in THF with a corresponding solution of 3-(4-(tert-butyl)phenyl)propanal to prepare the title product 1-butoxy-3-(4-(4-(tert-butyl)phenyl)but-1-en-1-yl)benzene.

6b: 1-butoxy-3-(4-(4-(tert-butyl)phenyl)-3-methylbut-1-en-1-yl)benzene

The procedure described in example 1.4 can be repeated by replacing the solution of 3-(4-isobutyl-2-methylphenyl)

propanal and 3-(2-isobutyl-4-methylphenyl)propanal in THF with a corresponding solution of 3-(4-(tert-butyl)phenyl)-2-methylpropanal to prepare the title product 1-butoxy-3-(4-(4-(tert-butyl)phenyl)-3-methylbut-1-en-1-yl)benzene.

6c: 1-butoxy-3-(4-(3-isopropylphenyl)pent-1-en-1-yl)benzene

The procedure described in example 1.4 can be repeated by replacing the solution of 3-(4-isobutyl-2-methylphenyl)propanal and 3-(2-isobutyl-4-methylphenyl)propanal in THF with a corresponding solution of 3-(3-isopropylphenyl)butanal to prepare the title product 1-butoxy-3-(4-(3-isopropylphenyl)pent-1-en-1-yl)benzene.

6d: 11-(3-butoxyphenyl)-2,6-dimethylundeca-6,10-dien-2-ol

The procedure described in example 1.4 can be repeated by replacing the solution of 3-(4-isobutyl-2-methylphenyl)propanal and 3-(2-isobutyl-4-methylphenyl)propanal in THF with a corresponding solution of 9-hydroxy-5,9-dimethyldec-4-enal to prepare the title product 11-(3-butoxyphenyl)-2,6-dimethylundeca-6,10-dien-2-ol.

6e: 1-butoxy-3-(3-methyldodec-1-en-1-yl)benzene

The procedure described in example 1.4 can be repeated by replacing the solution of 3-(4-isobutyl-2-methylphenyl)propanal and 3-(2-isobutyl-4-methylphenyl)propanal in THF with a corresponding solution of 2-methylundecanal to prepare the title product 1-butoxy-3-(3-methyldodec-1-en-1-yl)benzene.

6f: 5-(4-(3-butoxyphenyl)-2-methylbut-3-en-1-yl)benzo[d][1,3]dioxole

The procedure described in example 1.4 can be repeated by replacing the solution of 3-(4-isobutyl-2-methylphenyl)propanal and 3-(2-isobutyl-4-methylphenyl)propanal in THF with a corresponding solution of 3-(benzo[d][1,3]dioxol-5-yl)-2-methylpropanal to prepare the title product 5-(4-(3-butoxyphenyl)-2-methylbut-3-en-1-yl)benzo[d][1,3]dioxole.

6q: 1-butoxy-3-(tetradeca-1,3-dien-1-yl)benzene

The procedure described in example 1.4 can be repeated by replacing the solution of 3-(4-isobutyl-2-methylphenyl)propanal and 3-(2-isobutyl-4-methylphenyl)propanal in THF with a corresponding solution of tridec-2-enal to prepare the title product 1-butoxy-3-(tetradeca-1,3-dien-1-yl)benzene.

6h: 1-butoxy-3-(3-phenylprop-1-en-1-yl)benzene

The procedure described in example 1.4 can be repeated by replacing the solution of 3-(4-isobutyl-2-methylphenyl)propanal and 3-(2-isobutyl-4-methylphenyl)propanal in THF with a corresponding solution of 2-phenylacetaldehyde to prepare the title product 1-butoxy-3-(3-phenylprop-1-en-1-yl)benzene.

6i: 1-butoxy-3-((5E)-undeca-1,5-dien-1-yl)benzene

The procedure described in example 1.4 can be repeated by replacing the solution of 3-(4-isobutyl-2-methylphenyl)propanal and 3-(2-isobutyl-4-methylphenyl)propanal in THF with a corresponding solution of (E)-dec-4-enal to prepare the title product 1-butoxy-3-((5E)-undeca-1,5-dien-1-yl)benzene.

6j: 5-(5-(3-butoxyphenyl)pent-4-en-1-ylidene)octahydro-1H-4,7-methanoindene

The procedure described in example 1.4 can be repeated by replacing the solution of 3-(4-isobutyl-2-methylphenyl)propanal and 3-(2-isobutyl-4-methylphenyl)propanal in THF with a corresponding solution of 4-(octahydro-5H-4,7-methanoinden-5-ylidene)butanal to prepare the title product 5-(5-(3-butoxyphenyl)pent-4-en-1-ylidene)octahydro-1H-4,7-methanoindene.

6k: 1-butoxy-3-(4-(4-ethylphenyl)-3,3-dimethylbut-1-en-1-yl)benzene

The procedure described in example 1.4 can be repeated by replacing the solution of 3-(4-isobutyl-2-methylphenyl)propanal and 3-(2-isobutyl-4-methylphenyl)propanal in THF with a corresponding solution of 3-(4-ethylphenyl)-2,2-dimethylpropanal to prepare the title product 1-butoxy-3-(4-(4-ethylphenyl)-3,3-dimethylbut-1-en-1-yl)benzene.

6l: 1-butoxy-3-(7-methoxy-3,7-dimethylnon-1-en-1-yl)benzene

The procedure described in example 1.4 can be repeated by replacing the solution of 3-(4-isobutyl-2-methylphenyl)propanal and 3-(2-isobutyl-4-methylphenyl)propanal in THF with a corresponding solution of 6-methoxy-2,6-dimethyloctanal to prepare the title product 1-butoxy-3-(7-methoxy-3,7-dimethylnon-1-en-1-yl)benzene.

6m: 1-butoxy-3-(4-(4-isobutylphenyl)but-1-en-1-yl)benzene

The procedure described in example 1.4 can be repeated by replacing the solution of 3-(4-isobutyl-2-methylphenyl)propanal and 3-(2-isobutyl-4-methylphenyl)propanal in THF with a corresponding solution of 3-(4-isobutylphenyl)propanal to prepare the title product 1-butoxy-3-(4-(4-isobutylphenyl)but-1-en-1-yl)benzene.

EXAMPLE 7

Fragrance Comprising a Compound of Formula (I)

| Compound/Ingredient | parts by weight 1/1000 |
|---|---|
| Benzyl acetate | 15 |
| 2-(4-Methylcyclohex-3-en-1-yl)propan-2-yl acetate | 60 |
| (E)-2-Benzylideneoctanal | 30 |
| Decanal | 18 |
| Allyl 2-(isopentyloxy)acetate | 3 |
| CASSYRANE (2-(tert-butyl)-5-methyl-2-propyl-2,5-dihydrofuran) | 0.5 |
| Triethylcitrate (TEC) | 6.3 |
| Citronellol | 20 |
| CYCLAL C (2,4-dimethylcyclohex-3-ene-1-carbaldehyde) | 5 |
| Delta Damascone | 1 |
| (E)-dec-4-enal | 0.2 |
| DIHYDRO MYRCENOL | 60 |
| DPG | 296.3 |
| EUCALYPTUS essential oil | 10 |
| FLORALOZONE (3-(4-ethylphenyl)-2,2-dimethylpropanal) | 3 |

-continued

| Compound/Ingredient | parts by weight 1/1000 |
|---|---|
| FLORHYDRAL (3-(3-isopropylphenyl)butanal) | 2 |
| FRESKOMENTHE (2-(sec-butyl)cyclohexan-1-one) | 5 |
| GALBANONE (1-(3,3/5,5-dimethylcyclohex-1-en-1-yl)pent-4-en-1-one) | 4 |
| ISO E SUPER | 20 |
| ISOBUTAVAN (4-formyl-2-methoxyphenyl isobutyrate) | 0.2 |
| ISORALDEINE | 10 |
| JAVANOL | 1 |
| LABIENOXIME[1] 1%/IPM-TEC @ 10% DPG | 3 |
| LEMONILE (3,7-dimethylnona-2,6-dienenitrile) | 35 |
| Terpinolene (1-methyl-4-(propan-2-ylidene)cyclohex-1-ene) | 20 |
| Linalol | 90 |
| MANZANATE (ethyl 2-methylpentanoate) | 2 |
| METHYL PAMPLEMOUSSE (6,6-dimethoxy-2,5,5-trimethylhex-2-ene) | 5 |
| MYRALDENE (4-(4-methylpent-3-en-1-yl)cyclohex-3-ene-1-carbaldehyde) | 10 |
| NYMPHEAL™ (3-(4-isoputyl-2-methylpehnyl)propanal) | 8 |
| Orange terpenes | 240 |
| Petalia (2-cyclohexylidene-2-(o-tolyl)acetonitrile) | 7 |
| RHUBAFURAN (2,4-dimethyl-4-phenyltetrahydrofuran) | 0.5 |
| ROSYFOLIA ® (1-methyl-2-(5methylhex-4-en-2-yl)cyclopropyl)methanol | 3 |
| SYLKOLIDE ((E)-2-((3,5-dimethylhex-3-en-2-yl)oxy)-2-methylpropyl cyclopropanecarboxylate) | 5 |
| TOSCANOL (1-(cyclopropylmethyl)-4-methoxybenzene) | 1 |
| Total: | 1000 |

1) 3E,6E)-2,4,4,7-tetramethylnona-6,8-dien-3-one oxime

The fragrance composition above possesses a classical fresh green lemon character. This fragrance can be applied to, e.g., all-purpose cleaner (APC), at 0.1-1.5 wt % (e.g. 0.3 wt %).

By replacing 40 parts of DPG of the accord above by 3-butoxybenzaldehyde, i.e. a compound of formula (I), the overall odor character is now softer, more floral, rounder, and over all, the perception is easier, fresher, more comfortable.

By replacing 40 parts of DPG of the accord above by 3-butoxybenzaldehyde, i.e. a compound of formula (I), and replacing 110 parts of DPG of the accord above by a mixture comprising 1-butoxy-3-((1E,4Z)-hepta-1,4-dien-1-yl)benzene (60 parts) and two additional precursors (4-(dodecylthio)-4-methylpentan-2-one (10 parts) and ethyl N,S-bis(4-oxo-4-(2,6,6-trimethylcyclohex-3-en-1-yl)butan-2-yl) cysteinate (40 parts)), the longlastingness of the accord is greatly improved, delivering a pleasant and very natural combination.

EXAMPLE 8

Fragrance Comprising a Compound of Formula (II)

| Compound/Ingredient | parts by weight 1/1000 |
|---|---|
| Nerolex ((Z)-3,7-dimethylocta-2,6-dien-1-ol) | 11 |
| PETALIA (2-cyclohexylidene-2-(o-tolyl)acetonitrile) | 20 |
| LABIENOXIME 1%/IPM-TEC @ 10% DPG (3E,6E)-2,4,4,7-tetramethylnona-6,8-dien-3-one oxime) | 5 |
| Benzyl acetate | 15 |
| (Z)-hex-3-en-1-yl acetate | 2 |
| Myraldyle acetate | 20 |
| ((4-(4-methylpent-3-en-1-yl)cyclohex-3-en-1-yl)methyl acetate) | |
| 2-phenylethan-1-ol | 100 |
| (E)-2-benzylideneheptanal | 40 |
| (E)-2-benzylideneoctanal | 100 |
| dodecanal | 3 |
| ROSYFOLIA ® (1-methyl-2-(5methylhex-4-en-2-yl)cyclopropyl)methanol | 4 |
| NYMPHEAL ™ (3-(4-isoputyl-2-methylpehnyl)propanal) | 20 |
| Cyclamen aldehyde (3-(4-isopropylphenyl)-2-methylpropanal) | 30 |
| Indol @ 10% TEC | 7 |
| Prunolide (5-pentyldihydrofuran-2(3H)-one) | 2 |
| Peach Pure (5-heptyldihydrofuran-2(3H)-one) | 3 |
| Nectaryl (2-(2-(4-methylcyclohex-3-en-1-yl)propyl)cyclopentan-1-one) | 5 |
| Citronellol | 40 |
| Dipropylen glycol (DPG) | 195 |
| ESTRAGOLE (1-allyl-4-methoxybenzene) | 1 |
| HEDIONE (methyl 2-(3-oxo-2-pentylcyclopentyl)acetate) | 60 |
| Grapefruit oil | 20 |
| Isoeugenol | 9 |
| Citral | 3 |
| Linalol | 180 |
| FLOROCYCLENE (3a,4,5,6,7,7a-hexahydro-1H-4,7-methanoinden-6-yl propionate) | 10 |
| Geraniol | 45 |
| PEONILE ® (2-cyclohexylidene-2-phenylacetonitrile) | 50 |
| Total: | 1000 |

The fragrance composition above is a fresh floral green accord, reminiscent of fresh green muguet. This fragrance can be applied, e.g. in high density liquid detergent (HDLD), at 0.3-1.5 wt % (e.g. 0.6 wt %).

By replacing 30 parts of DPG of the accord above by 1-butoxy-3-((1E,4Z)-hepta-1,4-dien-1-yl)benzene, i.e. a precursor of a compound of formula (I), the fresh green effect on wet fabric is clearly enhanced. And, in particular, the longlastingness of the accord on dry fabric is clearly enhanced when the dry fabric is assessed after one or three days.

By replacing 70 parts of DPG of the accord above by 1-butoxy-3-((1E,4Z)-hepta-1,4-dien-1-yl)benzene, the green freshness becomes very present and brings a surprising and unusual freshness on dry fabric, reminiscent of green leaf and fresh apple skin.

EXAMPLE 9

Fragrance Comprising a Compound of Formula (II)

| Compound/Ingredient | parts by weight 1/1000 |
|---|---|
| 2-methyl-1-phenylpropan-2-yl acetate | 20 |
| 4-(tert-butyl)cyclohexyl acetate | 50 |
| (2-(1-ethoxyethoxy)ethyl)benzene | 2 |
| AGRUMEX (2-(tert-butyl)cyclohexyl acetate) | 25 |
| 2-phenylethan-1-ol | 10 |
| (E)-2-benzylideneoctanal | 100 |

-continued

| Compound/Ingredient | parts by weight 1/1000 |
|---|---|
| 2-methylundecanal | 1 |
| AMBROFIX (3a,6,6,9a-tetramethyldodecahydro-naphtho[2,1-b]furan) | 1 |
| methyl 2-aminobenzoate | 2 |
| AUBEPINE PARA CRESOL (4-methoxybenzaldehyde) | 3 |
| lemon terpens | 10 |
| Citronellol | 80 |
| delta damascone | 2 |
| DIHYDRO MYRCENOL | 100 |
| DIPHENYL OXIDE | 10 |
| DUPICAL (4-(octahydro-5H-4,7-methanoinden-5-ylidene)butanal) | 2 |
| EUCALYPTOL NATUREL | 3 |
| FLOROCYCLENE (3a,4,5,6,7,7a-hexahydro-1H-4,7-methanoinden-6-yl propionate) | 75 |
| GARDENOL (1-phenylethyl acetate) | 20 |
| ISO E SUPER | 100 |
| ISORALDEINE | 25 |
| JAVANOL @ 10% DPG | 5 |
| LEMONILE (3,7-dimethylnona-2,6-dienenitrile) | 2 |
| METHYL ACETOPHENONE (1-(p-tolyl)ethan-1-one) | 2 |
| 4-(tert-butyl)cyclohexan-1-ol | 10 |
| PATCHOULI ESS SANS FER INDONESIE ORPUR | 3 |
| PHARAONE (2-cyclohexylhepta-1,6-dien-3-one) 10%/DPG | 5 |
| Hexyl salicylate | 75 |
| SERENOLIDE (2-(1-(3,3-dimethylcyclohexyl)ethoxy)-2-methylpropyl cyclopropanecarboxylate) | 30 |
| SPIROGALBANONE (1-(spiro[4.5]dec-6/7-en-7-yl)pent-4-en-1-one | 1 |
| STEMONE ((Z)-5-methylheptan-3-one oxime) | 1 |
| TETRAHYDRO LINALOL | 50 |
| UNDECAVERTOL | 10 |
| Dipropylen glycol (DPG) | 165 |
| Total: | 1000 |

The fragrance composition above is a fresh floral green accord, reminiscent of fresh green muguet. This fragrance can be applied, e.g. in high density powder detergent (HDPD), at 0.1-1.5 wt % (e.g. 0.3 wt %).

By replacing 100 parts of DPG of the accord above by 1-butoxy-3-((1E,4Z)-hepta-1,4-dien-1-yl)benzene, i.e. a precursor of a compound of formula (I), the performance and diffusion on wet towels is enhanced with a fresh green pleasant character. And on dry fabric, the substantivity is noticeably improved, with an unusual and very pleasant fresh green character.

By replacing 110 parts of DPG of the accord above by a mixture comprising 1-butoxy-3-((1E,4Z)-hepta-1,4-dien-1-yl)benzene (70 parts) and two additional precursors (4-(dodecylthio)-4-methylpentan-2-one (10 parts) and ethyl N,S-bis(4-oxo-4-(2,6,6-trimethylcyclohex-3-en-1-yl)butan-2-yl)cysteinate (30 parts)), a very unusual and pleasant fresh green juicy fruity character is delivered on dry fabric. This fresh green juicy fruity character will lasts for few days, which is also novel and surprising.

The invention claimed is:

1. A method of using a compound of formula (I) as a fragrance

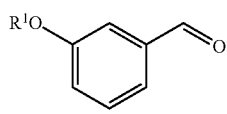
(I)

wherein $R^1$ is selected from linear or branched $C_3$-, $C_4$- and $C_5$-alkyl and $C_3$-, $C_4$- and $C_5$-alkenyl, the method comprising (a) mixing the compound of formula (I), or a precursor thereof, with a consumer product base, or (b) mixing a fragrance composition comprising the compound of formula (I), or a precursor thereof, with a consumer product base, (c) or entrapping the compound of formula (I) or a precursor thereof with an entrapment material and then mixing it with the consumer product base.

2. A method of using the compound of formula (I) as a fragrance

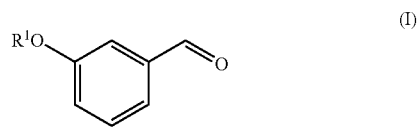
(I)

comprising the step of generating the compound of formula (I) by spontaneous air oxidation of a compound of formula (II)
wherein

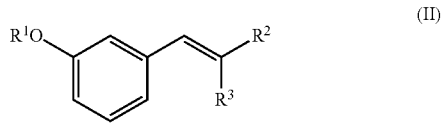
(II)

$R^1$ selected from linear or branched $C_3$-, $C_4$- and $C_5$-alkyl and $C_3$-, $C_4$- and $C_5$-alkenyl;

$R^2$ is selected from the group consisting of $C_4$-$C_{14}$ alkyl; $C_4$-$C_{14}$ alkyl substituted with one —OH group and/or up to two ether groups;

$C_4$-$C_{14}$ alkenyl; $C_4$-$C_{14}$ alkenyl substituted with one —OH group or an ether group;

$C_5$-$C_6$ cycloalkyl; $C_5$-$C_8$ cycloalkyl substituted with 1, 2, or 3 groups selected from $C_1$-$C_6$ alkyl and $C_2$-$C_4$ alkylidene;

$C_5$-$C_8$ cycloalkenyl; $C_5$-$C_8$ cycloalkenyl wherein the cycloalkenyl-ring is substituted with 1, 2, or 3 groups selected from $C_1$-$C_4$ alkyl, $C_2$-$C_4$ alkylidene, and $C_3$-$C_5$ cycloalkyl;

$(C_1$-$C_3)$alkyl$(C_5$-$C_6)$cycloalkyl wherein the cycloalkyl-ring is optionally substituted with one group selected from —OH group and =O group, and/or one or two ether group(s), and/or up to four $C_1$-$C_5$ alkyl groups;

$(C_1$-$C_4)$alkyl$(C_5$-$C_6)$cycloalkenyl wherein the cycloalkenyl-ring is optionally substituted with one —OH group, and/or one or two ether group(s), and/or up to four $C_1$-$C_5$ alkyl groups;

$(C_2$-$C_3)$alkenyl$(C_5$-$C_6)$cycloalkenyl wherein the cycloalkenyl-ring is optionally substituted with one —OH group, and/or one or two ether group(s), and/or up to four $C_1$-$C_5$ alkyl groups;

$(C_1$-$C_4)$alkyl$(C_6$-$C_{14})$aryl; $(C_1$-$C_4)$alkyl$(C_6$-$C_{14})$aryl wherein the aryl-ring is substituted with up to 2 groups selected from $C_1$-$C_4$ alkyl, —O—$CH_2$—O—, and —$OR^{12}$ wherein $R^{12}$ is independently selected from hydrogen and $C_1$-$C_4$ alkyl;

$(C_2$-$C_8)$alkenyl$(C_6$-$C_{14})$aryl; $(C_2$-$C_8)$alkenyl$(C_6$-$C_{14})$aryl wherein the aryl-ring is substituted with up to 2 groups selected from $C_1$-$C_4$ alkyl, —O—$CH_2$—O—, and —OR$^{13}$ wherein R$^{13}$ is independently selected from hydrogen and C$_1$-C$_4$ alkyl;

bi-, tri, or tetracyclic hydrocarbon ring comprising C$_8$-C$_{12}$ carbon atoms optionally substituted with up to 6 groups selected from C$_1$-C$_4$ alkyl, —O—CH$_2$—O—, and —OR$^{14}$ wherein R$^{14}$ is independently selected from hydrogen and C$_1$-C$_4$ alkyl; and R$^3$ is selected from hydrogen, C$_1$-C$_5$ alkyl, and C$_2$-C$_5$ alkenyl.

3. A compound of formula (II)

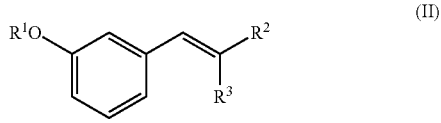

(II)

wherein

R$^1$ selected from linear or branched C$_3$-, C$_4$- and C$_5$-alkyl and C$_3$-, C$_4$- and C$_5$-alkenyl;

R$^2$ is selected from the group consisting of C$_4$-C$_{14}$ alkyl; C$_4$-C$_{14}$ alkyl substituted with one —OH group and/or up to two ether groups;

C$_4$-C$_{14}$ alkenyl; C$_4$-C$_{14}$ alkenyl substituted with one —OH group or an ether group;

C$_5$-C$_6$ cycloalkyl; C$_5$-C$_8$ cycloalkyl substituted with 1, 2, or 3 groups selected from C$_1$-C$_6$ alkyl and C$_2$-C$_4$ alkylidene;

C$_5$-C$_8$ cycloalkenyl; C$_5$-C$_8$ cycloalkenyl wherein the cycloalkenyl-ring is substituted with 1, 2, or 3 groups selected from C$_1$-C$_4$ alkyl, C$_2$-C$_4$ alkylidene, and C$_3$-C$_5$ cycloalkyl;

(C$_1$-C$_3$)alkyl(C$_5$-C$_6$)cycloalkyl wherein the cycloalkyl-ring is optionally substituted with one group selected from —OH group and =O group, and/or one or two ether group(s), and/or up to four C$_1$-C$_5$ alkyl groups;

(C$_1$-C$_4$)alkyl(C$_5$-C$_6$)cycloalkenyl wherein the cycloalkenyl-ring is optionally substituted with one —OH group, and/or one or two ether group(s), and/or up to four C$_1$-C$_5$ alkyl groups;

(C$_2$-C$_3$)alkenyl(C$_5$-C$_6$)cycloalkenyl wherein the cycloalkenyl-ring is optionally substituted with one —OH group, and/or one or two ether group(s), and/or up to four C$_1$-C$_5$ alkyl groups;

(C$_1$-C$_4$)alkyl(C$_6$-C$_{14}$)aryl; (C$_1$-C$_4$)alkyl(C$_6$-C$_{14}$)aryl wherein the aryl-ring is substituted with up to 2 groups selected from C$_1$-C$_4$ alkyl, —O—CH$_2$—O—, and —OR$^{12}$ wherein R$^{12}$ is independently selected from hydrogen and C$_1$-C$_4$ alkyl;

(C$_2$-C$_8$)alkenyl(C$_6$-C$_{14}$)aryl; (C$_2$-C$_8$)alkenyl(C$_6$-C$_{14}$)aryl wherein the aryl-ring is substituted with up to 2 groups selected from C$_1$-C$_4$ alkyl, —O—CH$_2$—O—, and —OR$^{13}$ wherein R$^{13}$ is independently selected from hydrogen and C$_1$-C$_4$ alkyl;

bi-, tri, or tetracyclic hydrocarbon ring comprising C$_8$-C$_{12}$ carbon atoms optionally substituted with up to 6 groups selected from C$_1$-C$_4$ alkyl, —O—CH$_2$—O—, and —OR$^{14}$ wherein R$^{14}$ is independently selected from hydrogen and C$_1$-C$_4$ alkyl; and R$^3$ is selected from hydrogen, C$_1$-C$_5$ alkyl, and C$_2$-C$_5$ alkenyl.

4. The compound according to claim 3 selected from
1-butoxy-3-((1E,4Z)-hepta-1,4-dien-1-yl)benzene;
1-butoxy-3-((1E,7Z)-deca-1,7-dien-1-yl)benzene;
1-(4-(3-butoxyphenyl)but-3-en-1-yl)-4-isobutyl-2-methylbenzene;
1-(4-(3-butoxyphenyl)but-3-en-1-yl)-2-isobutyl-4-methylbenzene;
1-(sec-butoxy)-3-((1E,4Z)-hepta-1,4-dien-1-yl)benzene;
1-((1E,4Z)-hepta-1,4-dien-1-yl)-3-(pentyloxy)benzene;
1-((1E,4Z)-hepta-1,4-dien-1-yl)-3-((2-methylallyl)oxy) benzene;
1-((1E,4Z)-hepta-1,4-dien-1-yl)-3-isopropoxybenzene;
1-butoxy-3-(4-(4-(tert-butyl)phenyl)but-1-en-1-yl)benzene;
1-butoxy-3-(4-(4-(tert-butyl)phenyl)-3-methylbut-1-en-1-yl)benzene;
1-butoxy-3-(4-(3-isopropylphenyl)pent-1-en-1-yl)benzene;
11-(3-butoxyphenyl)-2,6-dimethylundeca-6,10-dien-2-ol;
1-butoxy-3-(3-methyldodec-1-en-1-yl)benzene;
5-(4-(3-butoxyphenyl)-2-methylbut-3-en-1-yl)benzo[d][1,3]dioxole;
1-butoxy-3-(tetradeca-1,3-dien-1-yl)benzene;
1-butoxy-3-(3-phenylprop-1-en-1-yl)benzene;
1-butoxy-3-((5E)-undeca-1,5-dien-1-yl)benzene;
5-(5-(3-butoxyphenyl)pent-4-en-1-ylidene)octahydro-1H-4,7-methanoindene;
1-butoxy-3-(4-(4-ethylphenyl)-3,3-dimethylbut-1-en-1-yl)benzene;
1-butoxy-3-(7-methoxy-3,7-dimethylnon-1-en-1-yl)benzene; and
1-butoxy-3-(4-(4-isobutylphenyl)but-1-en-1-yl)benzene.

5. A method of fragrancing a consumer product, comprising adding to a consumer product base a compound of formula (I) as defined in claim 1, or precursor thereof.

6. The method according to claim 5, wherein the precursor of the compound of formula (I) is a compound of formula (II) as defined in claim 3.

7. The method according to claim 5, wherein the compound of formula (I) is generated by spontaneous air oxidation of a compound of formula (II) as defined in claim 3 when exposed to oxygen.

8. A consumer product comprising a compound of formula (I) as defined in claim 1, or a precursor thereof and a consumer product base.

9. The consumer product according to claim 8 wherein the consumer product is selected from home care products, personal care products and cleaning products.

10. A consumer product comprising a compound of formula (II) as defined in claim 2 and a consumer product base.

11. A consumer product comprising a compound of formula (II) as defined in claim 3 and a consumer product base.

12. The consumer product according to claim 10, wherein the consumer product is selected from home care products, personal care products and cleaning products.

13. The consumer product according to claim 11, wherein the consumer product is selected from home care products, personal care products and cleaning products.

14. A fragrance composition comprising a compound of formula (I) or a precursor thereof:

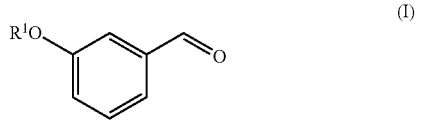

(I)

wherein $R^1$ is selected from linear or branched $C_3$-, $C_4$- and $C_5$-alkyl and $C_3$-, $C_4$- and $C_5$-alkenyl.

* * * * *